United States Patent [19]

Gluchowski

[11] Patent Number: 5,034,406

[45] Date of Patent: Jul. 23, 1991

[54] METHOD FOR REDUCING OR MAINTAINING INTRAOCULAR PRESSURE

[75] Inventor: Charles Gluchowski, Mission Viejo, Calif.

[73] Assignee: Allergan, Inc., Irvine, Calif.

[21] Appl. No.: 412,528

[22] Filed: Sep. 26, 1989

[51] Int. Cl.$^5$ ............................................. A61K 43/76
[52] U.S. Cl. ..................................... 514/377; 514/913
[58] Field of Search ................................ 514/377, 913

[56] References Cited

U.S. PATENT DOCUMENTS

| 3,598,833 | 8/1971 | Hiltmann et al. | |
| 3,676,798 | 7/1972 | Guilk et al. | 514/377 |
| 4,861,760 | 8/1989 | Mazuel et al. | 514/912 |

FOREIGN PATENT DOCUMENTS 675645  9/1967  South Africa.

OTHER PUBLICATIONS

Review: A Synopsis of Recent Developments in Antiglaucoma Drugs, Marsha A. McLaughlin and George C. Y. Chiou.

Editorial: Intraocular Pressure and Glaucoma, Alfred Sommer.

German Article: Stereochemische Untersuchungen uber Arzneimittel. 4 Mitt. (*) Konformation and antihypertensive Wirksamkeit von 2-(2,6-Dialkycyclohexyl-)-amino-2-oxazolinen (**) Hiltmann, Kurz, Wollweber and Stoepel.

*Primary Examiner*—Stanley J. Friedman
*Assistant Examiner*—Zohreh A. Fay
*Attorney, Agent, or Firm*—Gordon L. Peterson; Frank J. Uxa, Jr.

[57] ABSTRACT

A method of reducing or maintaining intraocular pressure in a mammalian eye, e.g., affected with glaucoma, is disclosed. This method comprises administering directly to the mammalian eye an effective amount of one or more 2-cycloalkylamino oxazolines, salts thereof, bases thereof and mixtures thereof.

26 Claims, No Drawings

METHOD FOR REDUCING OR MAINTAINING INTRAOCULAR PRESSURE

BACKGROUND OF THE INVENTION

The present invention relates to a method for reducing or maintaining intraocular pressure. More particularly, it relates to a method for reducing or maintaining intraocular pressure involving the administration of an effective amount of a 2-cycloalkylamino oxazoline and-/or a salt thereof and/or a base thereof, e.g., in an opthalmically acceptable carrier.

The method of the present invention is particularly useful for the management of glaucoma, a disease of the eye characterized by increased intraocular pressure. On the basis of its etiology, glaucoma has been classified as primary or secondary. For example, primary glaucoma in adults may be either chronic open-angle or acute or chronic angle-closure. Secondary glaucoma results from pre-existing ocular diseases such as uveitis, intraocular tumor or an enlarged cataract.

The underlying causes of primary glaucoma are not yet well known. The increased intraocular pressure is due to obstruction of aqueous humor outflow. In chronic open-angle glaucoma, the anterior chamber and its anatomic structures appear normal, but drainage of the aqueous humor is impeded. In acute and chronic angle-closure glaucoma, the anterior chamber is shallow, the filtration angle is narrowed and the iris may obstruct the trabecular meshwork at the entrance to the canal of Schlemm. Dilation of the pupil may push the root of the iris forward against the angle or may produce pupillary block and thus precipitate an acute attack. Eyes with narrow anterior chamber angles are predisposed to acute angle-closure glaucoma attacks of varying degrees of severity.

Secondary glaucoma is caused by any interference with the flow of aqueous humor from the posterior chamber into the anterior chamber and, subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptomatic for years before progressing to rapid loss of vision. In cases where surgery is not indicated, topical beta-adrenoceptor antagonists have traditionally been the drugs of choice for treating glaucoma Hiltmann et al U.S. Pat. No. 3,598,833 discloses 2-cycloalkylamino oxazolines as having local anesthetic properties, sedative properties, vasoconstrictory effects, mucous membrane deswelling properties, blood pressure depressant effects, and inhibitory effects on the secretion of gastric fluid. None of these properties and effects involve administering the 2-cycloalkylamino oxazoline directly to the eye. Further, there is no suggestion in the Hiltmann et al patent that such compounds are useful in reducing or maintaining intraocular pressure.

SUMMARY OF THE INVENTION

A new method for reducing or maintaining the intraocular pressure in a mammalian eye has been discovered. This method comprises administering directly to a mammalian eye an effective amount of one or more 2-cycloalkylamino oxazolines (as defined herein), salts thereof, bases thereof and mixtures thereof This new method is particularly effective in the treatment or management of mammalian, e.g., human, eyes affected with glaucoma.

DETAILED DESCRIPTION OF THE INVENTION

The 2-cycloalkylamino oxazolines, salts thereof and bases thereof which are administered directly to a mammalian eye in the present method are those which are effective to reduce or maintain, preferably to reduce, the intraocular pressure in the mammalian eye. The effective compounds are selected from the group consisting of:

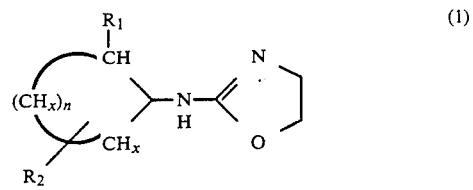

wherein $R_1$ is selected from the group consisting of alkyl radials containing 1 to 3 carbon atoms, $R_2$ is selected from the group consisting of H and alkyl radicals containing 1 to 5 carbon atoms, n is an integer in the range of 2 to 4, each x is independently selected from the integers 1 and 2, and each of the carbon atoms in the hydrocarbon ring has 4 bonds associated therewith; (1) in which the hydrocarbon ring includes one double bond in a position other than the alpha-beta position; salts thereof; bases thereof and mixtures thereof. All stereoisomers, tautomers and mixtures thereof which comply with the constraints of one or more formulae of the presently useful compounds set forth herein are included within the scope of the present invention.

The present method is particularly effective in a strategy for the treatment or management of glaucoma, whether primary or secondary glaucoma In this embodiment, one or more of the presently useful compounds are preferably administered directly to a mammalian eye affected with glaucoma to effectively reduce or maintain, preferably control, the intraocular pressure in the glaucoma-affected eye.

Although the hydrocarbon ring of the presently useful compounds may include 5, 6 or 7 carbon atoms, it is preferred that this ring contain 6 carbon atoms. Thus, with regard to the above-noted structural formulae, n is preferably 3. Also, this ring may include one double bond at a position other than the alpha-beta position However, it is preferred that the hydrocarbon ring be completely saturated.

In one particularly useful embodiment, the $R_2$ group is situated on the last carbon atom of the hydrocarbon ring. For example, with regard to a 6 member hydrocarbon ring, compound (1) preferably has the following formula:

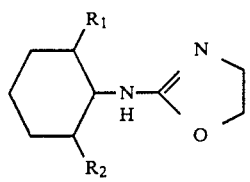

Although both $R_1$ and $R_2$ can be alkyl radicals, very useful reductions in intraocular pressure are obtained using compounds in which $R_1$ is an alkyl radical and $R_2$ is an H radical.

Quite often the presently useful compounds are present as a mixture of enantiomers or optical isomers. While there are differences in activity, e.g., intraocular pressure reducing activity, between optical isomers, such differences often do not warrant the effort and expense required to produce or separate an individual optical isomer. Thus, a mixture of enantiomers is useful even where there is a difference in the activities of the individual enantiomers. However, each individual enantiomer having the requisite activity is useful in the present method and is included within the scope of the present invention.

Regarding geometric isomerism it is preferred that the $R_1$ group be trans relative to the amino oxazoline group of (1) above. In the event that the $R_1$ and $R_2$ groups are both alkyl groups and $R_2$ is situated on the last carbon atom of the hydrocarbon ring, it is preferred that both $R_1$ and $R_2$ be trans relative to the amino oxazoline group of (1) above. Such trans isomers have been found to be particularly effective in reducing intraocular pressure. In certain instances, the corresponding cis isomers have little or no intraocular pressure reducing activity. Therefore, it may be advantageous to selectively produce or separate one or more geometric isomers, e.g., the above-noted trans isomers, in order to obtain the desired intraocular pressure reducing activity.

The presently useful compounds are often administered to the eye in the form of a mixture with an ophthalmically acceptable carrier. Any suitable, e.g., conventional, ophthalmically acceptable carrier may be employed. Such a carrier is ophthalmically acceptable if it has substantially no long term or permanent detrimental effect on the eye to which it is administered. Examples of ophthalmically acceptable carriers include water, in particular distilled water, saline and the like aqueous media. The presently useful compounds are preferably administered to the eye as a liquid mixture with the carrier. The compounds are more preferably soluble in the carrier so that the compounds are administered to the eye in the form of a solution.

When an ophthalmically acceptable carrier is employed, it is preferred that the mixture contain one or more of the presently useful compounds in an amount in the range of about 0.0001% to about 1%, more preferably about 0.05% to about 0.5%, W/V.

Any method of administering drugs directly to a mammalian eye may be employed to provide the presently useful compound or compounds to the eye to be treated. By the term "administering directly" is meant to exclude those general systemic drug administration modes, e.g., injection directly into the patients blood vessels, oral administration and the like, which result in the compound or compounds being systemically available. The primary effect on the mammal resulting from the direct administering of the presently useful compound or compounds to the mammal's eye is preferably a reduction in intraocular pressure. More preferably, the presently useful compound or compounds are applied topically to the eye or are injected directly into the eye. Particularly useful results are obtained when the compound or compounds are applied topically to the eye.

Topical ophthalmic preparations, for example ocular drops, gels or creams, are preferred because of ease of application, ease of dose delivery, and fewer systemic side effects, such as cardiovascular hypotension. An exemplary topical ophthalmic formulation is shown below in Table I. The abbreviation q.s. means a quantity sufficient to effect the result or to make volume.

TABLE I

| Ingredient | Amount (% W/V) |
| --- | --- |
| 2-Cycloalkylamino oxazoline | about 0.0001 to about 1.0 |
| Preservative | 0-0.10 |
| Vehicle | 0-40 |
| Tonicity Adjustor | 1-10 |
| Buffer | 0.01-10 |
| pH Adjustor | q.s. pH 4.5-7.5 |
| antioxidant | as needed |
| Purified Water | as needed to make 100% |

Various preservatives may be used in the ophthalmic preparation described in Table I above. Preferred preservatives include, but are not limited to, benzalkonium chloride, chlorobutanol, thimerosal, phenylmercuric acetate, and phenylmercuric nitrate. Likewise, various preferred vehicles may be used in such ophthalmic preparation. These vehicles include, but are not limited to, polyvinyl alcohol, povidone, hydroxypropyl methyl cellulose, poloxamers, carboxymethyl cellulose, hydroxyethyl cellulose, and purified water.

Tonicity adjustors may be added as needed or convenient. They include, but are not limited to, salts, particularly sodium chloride, potassium chloride, mannitol, and glycerin, or any other suitable ophthalmically acceptable tonicity adjustor.

Various buffers and means for adjusting pH may be used so long as the resulting preparation is ophthalmically acceptable. Accordingly, buffers include, but are not limited to, acetate buffers, citrate buffers, phosphate buffers, and borate buffers. Acids or bases may be used to adjust the pH of these formulations as needed.

In a similar vein, ophthalmically acceptable antioxidants include, but are not limited to, sodium metabisulfite, sodium thiosulfate, acetylcysteine, butylated hydroxyanisole, and butylated hydroxytoluene.

Other excipient components which may be included in the exemplary ophthalmic preparation described in Table I are chelating agents which may be added as needed. The preferred chelating agent is edetate disodium, although other chelating agents may also be used in place of or in conjunction with it.

The presently useful 2-cycloalkylamino oxazolines may be prepared by reacting 2-cycloalkyl-isocyanide dichlorides of the formula:

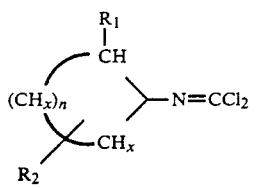

with ethanolamine in organic solvents or in water, and if desired, with the addition of a base such as triethylamine, sodium carbonate or sodium hydroxide at a temperature of from 0° C. to 100° C. Alternatively, these compounds can be prepared by cyclizing reactive esters of N'-cycloalkyl 1-N'-beta-hydroxy-ethyl-ureas of the formula:

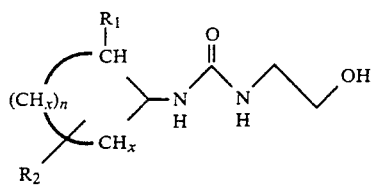

by heating in water, optionally at temperatures above 100° C. under pressure and precipitating the bases by means of ammonia from the resultant aqueous solution of the 2-cycloalkylamino oxazoline salts formed. Additionally, N'-cycloalkyl 1-N'-beta-chloro-ethyl-ureas of the formula

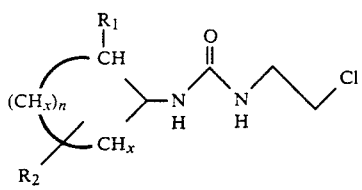

can be cyclized by heating, in an aqueous suspension or in refluxing ethanol solvent, to form the corresponding 2-cycoalkylamino oxazolines. $R_1$, $R_{2,x}$ and n have the meanings set forth above. The hydrocarbon ring may contain a double bond, with the proviso that if there is a double bond, such is not in the alpha-beta position. Such compounds which include a double bond may be prepared by methods analogous to those given above.

If desired the salts so obtained can be converted into the free bases by means of a base such as a sodium hydroxide solution or ammonia.

A more detailed description of certain methods for the synthesis of the presently useful compounds is set forth in Hiltmann et al U.S. Pat. No. 3,598,833 which is hereby incorporated in its entirety by reference herein.

The following non-limiting examples illustrate certain aspects of the present invention.

EXAMPLES 1 TO 8

A series of eight (8) 2-cycloalkylamino oxazolines were selected for testing. These materials, each except for the material used in Examples 7 and 8 being a mixture of enantiomers, were as follows:

1. 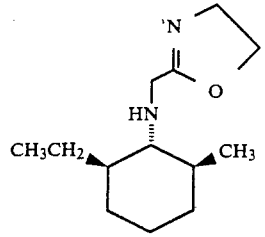

2. 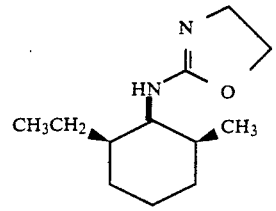

3. 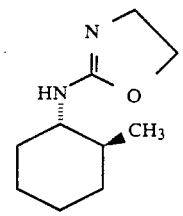

4. 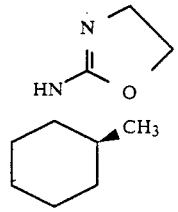

5. 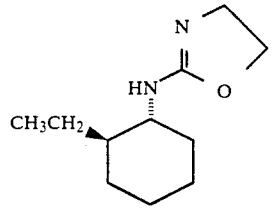

6. 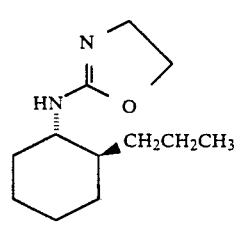

7. 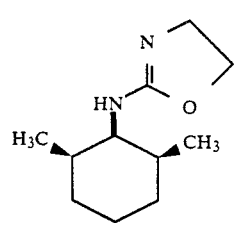

-continued

8.

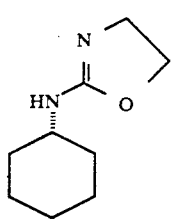

In addition the individual enantiomers of the mixture tested in Example 5 were tested These individual enantiomers are identified as (+) enantiomer (Example 5A) and (−) enantiomer (Example 5B).

Each of these materials was dissolved in distilled water at a concentration of 0.1% (W/V). Each of these solutions was administered topically and unilaterally to one eye of a drug-naive, unanesthetized New Zealand white rabbit in a single 50 micro liter drop. The contralateral eye received an equal volume of saline prior to determining the intraocular pressure after the mixture was administered. Also, approximately 10 micro liters of 0.5% (W/V) proparacaine (topical anesthetic) was applied to the corneas of each of the rabbits before determining intraocular pressure. As a control test, six (6) other drug-naive, unanesthetized New Zealand white rabbits were treated and tested as described above except that no 2-cycloalkylamino oxazoline was included in the solutions administered to the eyes.

The intraocular pressure was determined in both eyes of each rabbit both before and after the solutions were administered. Such intraocular pressure determinations were made in the conventional manner using conventional equipment.

Results of these IOP determinations were as follows:

| Example | Maximum Difference in Intraocular Pressure After Solution Administration mm Hg | |
|---------|---------------------------|---------------------------|
|         | Ipsilateral (Treated) Eye | Contralateral (Untreated) Eye |
| Control | N.S. | N.S. |
| 1 | −3.8 ± 0.9 | −6.6 ± 0.9 |
| 2 | N.S. | N.S. |
| 3 | −2.4 ± 0.8 | −3.3 ± 1.2 |
| 4 | N.S. | N.S. |
| 5 | −5.0 ± 1.3 | −5.4 ± 1.4 |
| 5A | −6.6 ± 1.6 | −5.5 ± 1.0 |
| 5B | −3.2 ± 0.6 | −3.0 ± 0.3 |
| 6 | −6.0 ± 1.1 | −8.3 ± 1.6 |
| 7 | N.S. | N.S. |
| 8 | N.S. | N.S. |

N.S. refers to no significant change in the intraocular pressure.

These results demonstrate the effectiveness in reducing intraocular pressure achieved by directly administering 2-cycloalkylamino oxazolines to mammalian eyes. Particularly useful results, Examples 1, 3, 5, 5A, 5B and 6, were obtained using 2-cycloalkylamino oxazolines in which the alkyl substituent group or groups on the hydrocarbon ring is trans relative to the amino oxazoline group. In addition, at least with regard to certain mammalian eyes, e.g., New Zealand white rabbit eyes, the intraocular pressure in the contralateral eye is also reduced, often to a greater extent then observed in the ipsilateral eye. Examples 5A and 5B demonstrate that both of the individual enantiomers have intraocular pressure reducing activity, although to differing degrees. Further, the 2-cycloalkylamino oxazoline mixture used in Example 6 was found to be particularly useful in reducing intraocular pressure while having less sedative effect than the mixtures used in Examples 1, 3 and 5. The results of these tests demonstrate that 2-cycloalkylamino oxazolines can be directly administered to mammalian eyes to reduce or maintain intraocular pressure, e.g., in the treatment of mammalian eyes affected with glaucoma.

While this invention has been described with respect to various specific examples and embodiments, it is to be understood that the invention is not limited thereto and that it can be variously practiced within the scope of the following claims.

I claim:

1. A method for reducing or maintaining the intraocular pressure in a mammalian eye comprising administering directly to a mammalian eye in an amount effective to reduce or maintain the intraocular pressure in the mammalian eye of a compound selected from the group consisting of:

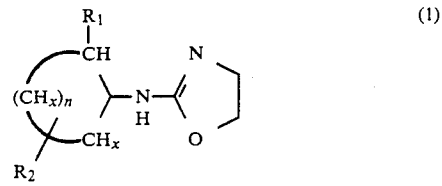

wherein $R_1$ is selected from the group consisting of alkyl radials containing 1 to 3 carbon atoms, $R_2$ is selected from the group consisting of H and alkyl radicals containing 1 to about 5 carbon atoms, n is an integer in the range of 2 to 4, each x is independently selected from the integers 1 and 2, and each of the carbon atoms in the hydrocarbon ring has 4 bonds associated therewith; (1) in which the hydrocarbon ring includes a double bond in a position other than the alpha-beta position; salts thereof; bases thereof and mixtures thereof.

2. The method of claim 1 wherein said compound is administered directly to the mammalian eye in an amount effective in reduce the intraocular pressure in the mammalian eye.

3. The method of claim 1 wherein said administering includes at least one of applying said compound topically to the mammalian eye and injecting said compound directly into the mammalian eye.

4. The method of claim 1 wherein said compound is administered in the form of a mixture with an ophthalmically acceptable carrier.

5. The method of claim 4 wherein said mixture is a liquid at the time of said administering.

6. The method of claim 4 wherein said compound is present in said mixture in an amount in the range of about 0.0001% to about 1% (W/V).

7. The method of claim 4 wherein said compound is present in said mixture in an amount in the range of about 0.05% to about 0.5% (W/V).

8. The method of claim 1 wherein the mammalian eye is affected with glaucoma.

9. The method of claim 1 wherein n is equal to 3.

10. The method of claim 1 wherein said compound is selected from the group consisting of (1), salts thereof, bases thereof and mixtures thereof.

11. The method of claim 10 wherein (1) has the following formula:

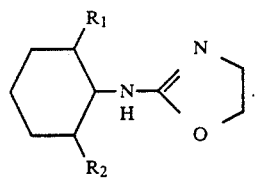

12. The method of claim 1 wherein $R_2$ is H.
13. The method of claim 11 wherein $R_2$ is H.
14. The method of claim 1 wherein said compound is a mixture of enantiomers.
15. The method of claim 13 wherein said compound is a mixture of enantiomers.
16. The method of claim 1 wherein $R_1$ is trans relative to the amino oxazoline group of (1).
17. The method of claim 11 wherein $R_1$ is trans relative to the amino oxazoline group of (1).
18. The method of claim 13 wherein $R_1$ is trans relative to the amino oxazoline group of (1).
19. The method of claim 1 wherein said compound has the following formula:

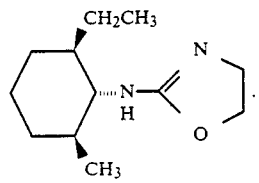

20. The method of claim 19 wherein said compound is a mixture of enantiomers.
21. The method of claim 1 wherein said compound has the following formula:

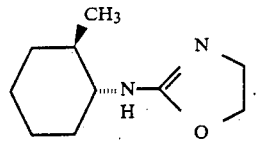

22. The method of claim 21 wherein said compound is a mixture of enantiomers.
23. The method of claim 1 wherein said compound has the following formula:

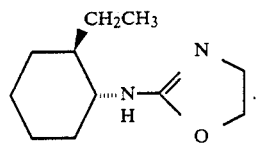

24. The method of claim 23 wherein said compound is a mixture of enantiomers.
25. The method of claim 1 wherein said compound has the following structure:

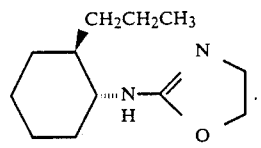

26. The method of claim 25 wherein said compound is a mixture of enantiomers.

* * * * *

UNITED STATES PATENT AND TRADEMARK OFFICE
CERTIFICATE OF CORRECTION

PATENT NO. : 5,034,406
DATED : July 23, 1991
INVENTOR(S) : Charles Gluchowski

It is certified that error appears in the above-identified patent and that said Letters Patent is hereby corrected as shown below:

Col. 1, line 52 after "glaucoma" insert a period.

Col. 2, line 60 after the second occurance of "position" insert a period.

Col. 7, line 13 after the second occurence of "tested" insert a period.

Col. 8, line 33 change "radials" to -- radicals --.

Col. 8, line 45 change "in reduce" to -- to reduce --.

Col. 6, lines 31-40 delete the formula of Example 4 and replace with the following:

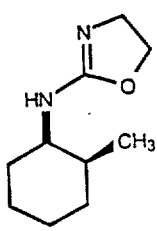

Signed and Sealed this

Fourth Day of May, 1993

Attest:

MICHAEL K. KIRK

Attesting Officer

Acting Commissioner of Patents and Trademarks